United States Patent

Bishop

Patent Number: 6,014,209
Date of Patent: *Jan. 11, 2000

[54] METHOD OF OPTICALLY INSPECTING MULTI-LAYERED ELECTRONIC PARTS AND THE LIKE WITH FLUORESCENT SCATTERING TOP LAYER DISCRIMINATION AND APPARATUS THEREFOR

[75] Inventor: Robert Bishop, Newton, Mass.

[73] Assignee: Beltronics, Inc., Newton, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/880,836

[22] Filed: Jun. 23, 1997

[51] Int. Cl.[7] .................................................. G01N 21/88
[52] U.S. Cl. ............................................................ 356/237.5
[58] Field of Search .................................. 356/237, 237.5

[56] References Cited

U.S. PATENT DOCUMENTS

| | | | |
|---|---|---|---|
| 5,053,626 | 10/1991 | Tillotson | 356/417 |
| 5,278,012 | 1/1994 | Yamanaka et al. | 356/237 |
| 5,324,401 | 6/1994 | Yeung et al. | 356/344 |
| 5,455,998 | 10/1995 | Miyazono et al. | 29/611 |

*Primary Examiner*—F. L. Evans
*Attorney, Agent, or Firm*—Rines And Rines

[57] ABSTRACT

A novel optical inspection technique for multi-layer wafers and the like in which conductor patterns of a top layer only are to be inspected, such layer being upon an intermediate transparent or translucent insulation layer in turn upon a base layer(s) thereunder, wherein the intermediate layer only is fluoresced, displaying the top layer conductors as dark in the field of fluorescent light, and causing reflections from layers below the intermediate layer effectively to disappear to obviate confusion with the top layer conductors to be inspected.

12 Claims, 4 Drawing Sheets

METHOD OF OPTICALLY INSPECTING MULTI-LAYERED ELECTRONIC PARTS AND THE LIKE WITH FLUORESCENT SCATTERING TOP LAYER DISCRIMINATION AND APPARATUS THEREFOR

The present invention relates to the optical inspection of electronic parts and the like, being more particularly directed to multi-layered electronic parts such as those used for wafers from which integrated circuit chips are formed, flat display panels, multi-chip modules, and flexible circuit patches and decals, etc., wherein there are top layers of conductors in various patterns, an intermediate layer (sometimes externally carrying the conductor layer on top) and comprising transparent or translucent insulation, and base substrate or bottom layers as of ceramic, glass, metal and the like, also often carrying conductors in various patterns.

BACKGROUND

Fluorescent light emissions have previously been used to inspect electronic circuit boards consisting of layers of epoxy containing conductors defining circuits deposited therein. The conductors are generally metal that can have a very rough finish, such as copper, oxidized copper, reflowed copper with a tin covering and the like, wherein the rough surfaces prove to difficult properly optically image to inspect for defects. As a result, manufacturers of inspection equipment have employed lasers of wavelength suitable selectively fluoresce the epoxy layer carrying the conductors comprising the electronic circuit. In doing this, the epoxy background fluoresces in a different wavelength (color) while the conductors do not fluoresce and thus appear dark. If the conductors have defects such as broken conductors, such defects will accordingly appear as non-dark areas and can be located. Likewise, shorts appear dark where a bright region should be, and are thereby detected as defects. The importance for this use of the fluorescence is specifically to overcome the effects of the optical variations or imaging imperfections in the rough conductor lines themselves.

In an article entitled "Digital Optical Imaging Of Benzo-Cyclobritene (BCB) Thin Films On Silicon Wafers", by R. A. DeVries et al, Mat. Resi. Soc. Symp Proc. Vol 381, 1995, pages 165–173, thin films have been fluoresced to reveal thickness variations or particles and the like.

Fluorescence has also been used to detect various cracks and imperfections in machine parts and the like, wherein fluorescent material is washed on the part and then wiped off, so that the only place that the fluorescent material remains is in a crack or defect into which the fluorescent material has seeped.

In connection with the dense multi-layer integrated circuit parts of concern in connection with the present invention, on the other hand, where several layers or coatings are superimposed upon a bottom base substrate layer that itself may contain conductor lines and upon which a transparent or translucent intermediate insulation layer is superposed, in turn carrying a top layer containing patterns of conductors to be inspected for defects, a very different problem arises in the optical inspecting of such multi-layered parts for such defects and the like. This problem resides from the compounding of reflections from all the superposed layers since the reflected incident light reflects from the lower layers as well as the top layer, creating an overlay of all these reflections which does not allow discriminating inspection of just the top conductor pattern layer alone, as required.

Attempts to discriminate the top conductor pattern images by the use of dark fields, shallow angle illumination, color discrimination, and cross polarization illumination have not met with success.

Underlying the present invention, however, is the discovery that through the use of an intermediate light transmitting preferably translucent or transparent insulating layer that is susceptible, in response to a predetermined wavelength of incident light, to fluorescing at a different wavelength, the conductors of the conductor pattern of the top layer reflect the incident light at its original wavelength and do not fluoresce, and can be readily distinguished, and the desired inspection of the top layer conductors only can be discriminatingly and selectively achieved, while also rejecting, masking or making disappear, any incident light reflections from layers below the intermediate fluorescing layer, admirably solving the above-mentioned problem.

OBJECTS OF INVENTION

The primary object of the present invention, accordingly, is to provide a new and improved method of and apparatus for enabling the discriminating and selective optical inspection of defects and the like of top layers of a multi-layered electronic part and the like comprising also intermediate and bottom layers, wherein the top layer includes a pattern of conductors, such as lines and the like to be discriminatingly inspected for such defects, and in which the intermediate layer comprises transparent or somewhat translucent insulation susceptible to fluorescing in response to the predetermined incident wavelength of inspection light, selectively displaying the top conductors as dark images on the fluorescing intermediate layer image, and with the fluorescing image masking reflections from lower layers.

A further object is to provide such a novel optical inspection technique wherein the inspecting of top layers with conductors and the like is selectively enabled to be imaged while effectively causing reflections from layers including conductors therebelow, effectively totally to disappear.

Other and further objects will be explained hereinafter and are more particularly delineated in the appended claims

SUMMARY

In summary, however, from perhaps one of its broadest viewpoints, the invention embraces a method of optically inspecting a top layer of a multi-layered electronic part comprising also intermediate and bottom layers, the top layer including a pattern of, conductors to-be-inspected and an intermediate layer comprising transparent or translucent insulation, the method involving selecting a predetermined wavelength of incident light to which the intermediate insulation layer and not the conductors or other layers responds by fluorescing at a different wavelength, and impinging the incident light upon the top layer of the part, reflecting the incident light from the layers and returning the reflections back to an inspection camera, returning fluorescing light of said different wavelength to the camera from the fluorescing intermediate layer, selectively imaging only the returned fluorescing light to suppress all other incident light reflections to the camera from layers above and below the intermediate layer, thereby to present the non-fluorescing pattern of conductors of the top layer as contrastingly dark in a background of the fluorescing intermediate layer image, with reflections from below the intermediate layer effectively disappearing.

Preferred design techniques and best mode of operation are hereinafter described in detail.

DRAWINGS

The invention will now be described in connection with the accompanying drawings, FIGS. 1A and 1B of which are partial cross sectional views showing light reflection from a multi-layer chip or the like back to a camera in accordance with the techniques of the present invention, the chip in FIG. 1B having been moved in scanning to the left, in front of the camera from the position of FIG. 1A;

Figure 3:
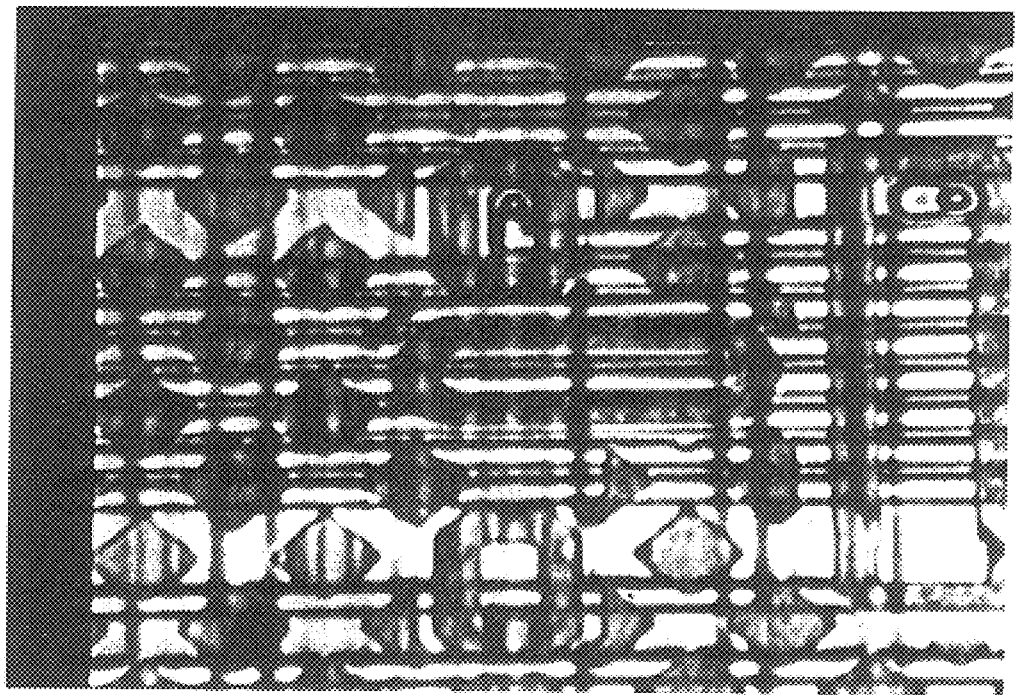
FIG. 3 is a view of the overlaying intermingled and indistinguishable reflections occurring from various layers of a multi-layer wafer prior to the present invention and which renders the discriminating detection of defects in just the top layer substantially impossible.
Figure 4:
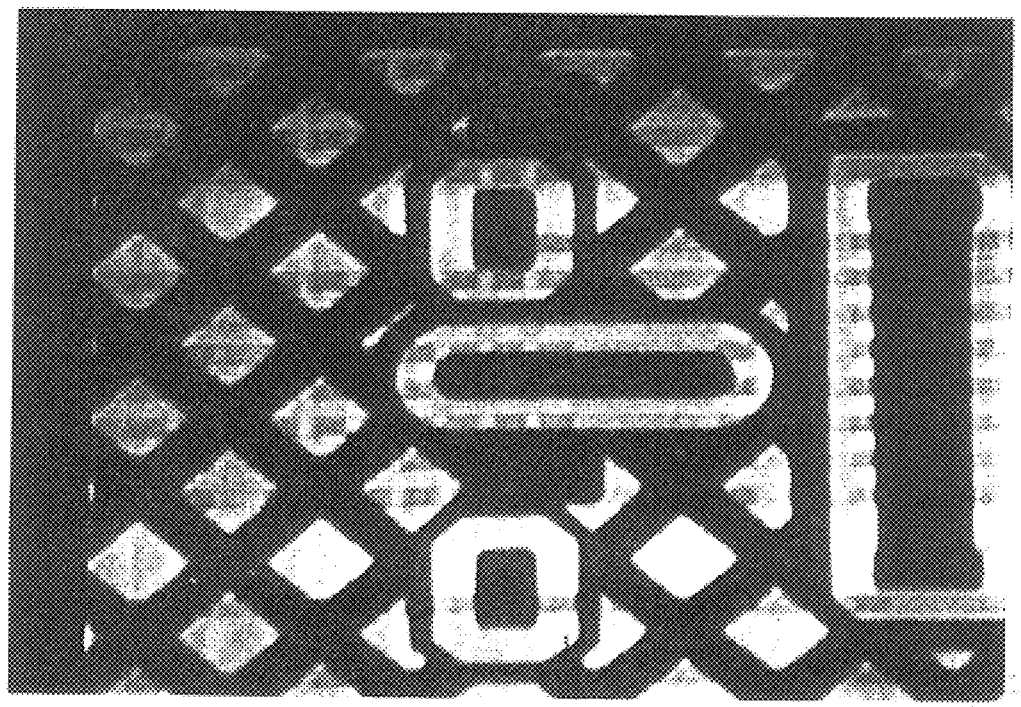
Figure 5:
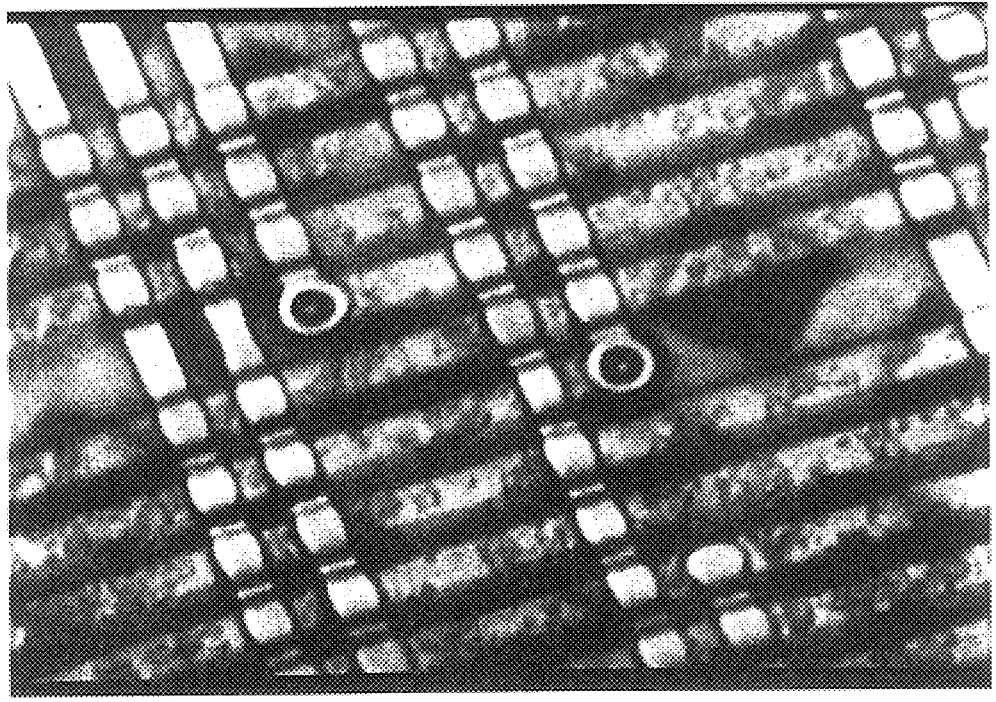
Figure 6:
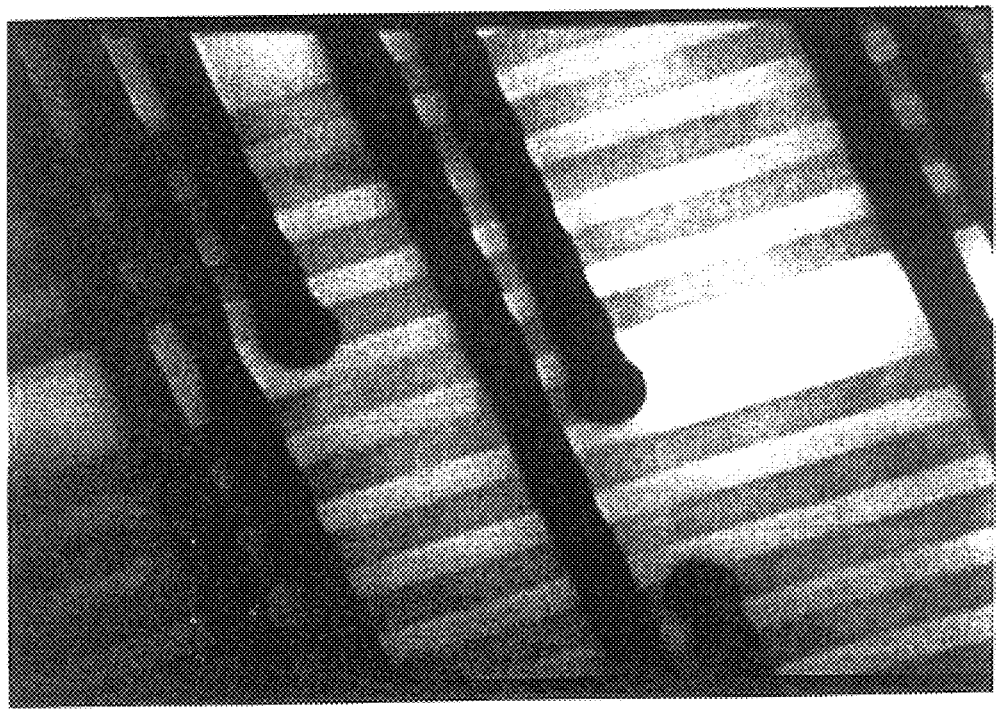

FIG. 4 is the imaging with the selection of the fluorescing intermediate insulation layer in accordance with the invention showing a total solution to the problem of selectively indicating the top layer pattern of conductors and suppressing all reflections below the intermediate layer; and FIGS. 5 and 6 are respectively similar to FIGS. 3 and 4 for a different wafer, again showing the efficacy of the invention.

PREFERRED EMBODIMENT(S) OF THE INVENTION

Figure 1A:
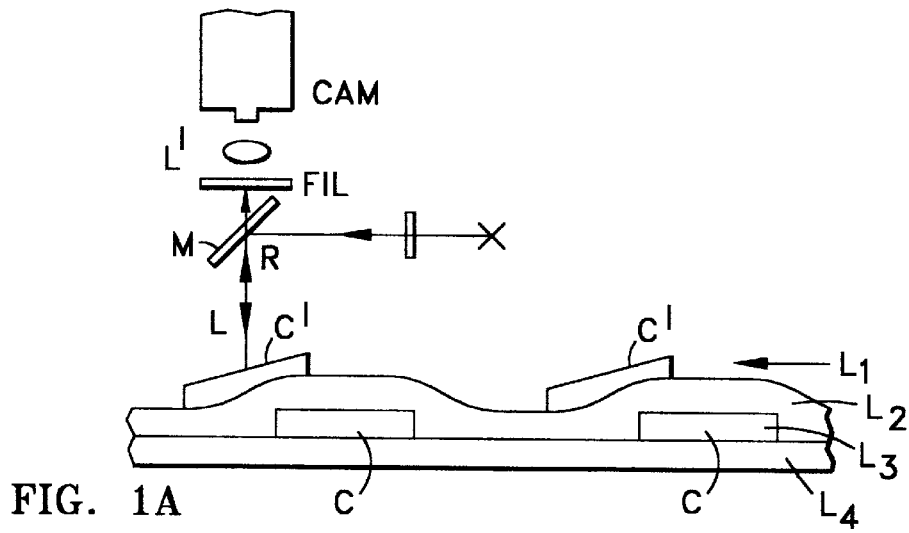
FIG. 1C is a similar view at a next scanning position showing fluorescent scatter back to the camera from the intermediate layer only.
Figure 1B:
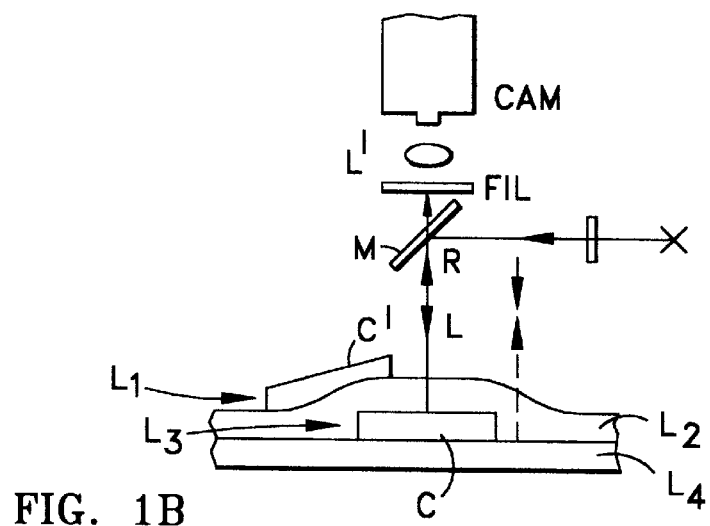
Figure 1C:
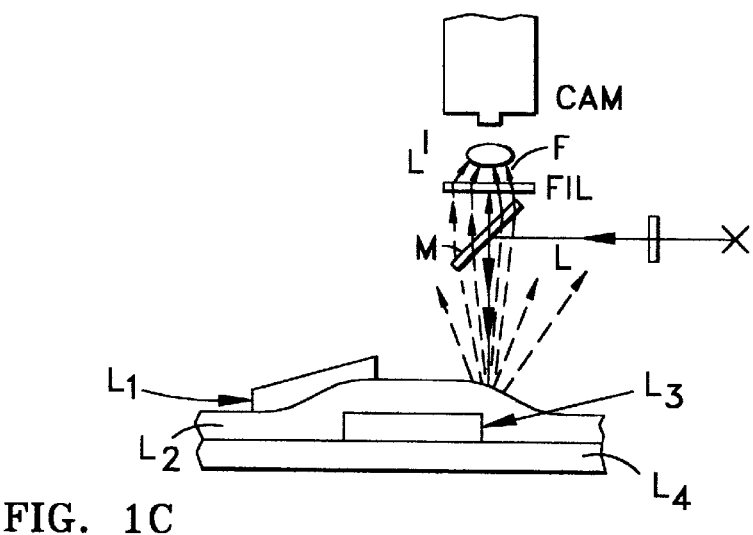

A typical multi-layer chip of the character above-described is shown in FIGS. 1A–C, comprising a base or substrate layer $L_4$ as of ceramic, for example, shown carrying a layer $L_3$ of metal conductors C thereupon, and in turn covered by an intermediate layer $L_2$, generally preferably translucent or transparent as, for example, of organic polyimid material and the like, which insulates the lower layer conductors C from further conductors $C^1$ on a top layer $L_1$ superposed upon the intermediate insulating layer $L_2$.

Incident light L from a light source is illustrated as directed by a half-silvered mirror M upon the top layer $L_1$ of the chip and reflects from the top layer pattern of conductors $C^1$. The solid vertical arrowed lines indicate light-illuminating incidence L and reflection R back towards the inspection camera CAM. Since the intermediate insulation layer $L_2$ covering the lower conductors C of the layer $L_3$ will not be flat but irregular with bumps, as shown, the top conductors $C^1$ may be somewhat angled by the projecting irregularities or bumps in layer $L_2$, as shown, and some reflection therefrom will not reach the camera in view of the angle of the deposited layer of conductor $C^1$; but flat regions of the conductor $C^1$ will be reflected back at R up toward the inspection camera. In view of the light transmitting properties of the translucent or transparent intermediate insulation layer $L_2$, light will also reflect back towards the camera CAM from the lower layer conductors C, FIG. 1B, and from the base layer $L_4$. This causes a composite of overlying reflections from the various layers that confusingly makes inspection of the top layer conductors only quite difficult if not impossible in many cases as will later be more fully explained.

The camera and imaging circuitry may be for example of the type described in my prior U.S. Letters Patent Nos. 5,119,434 and 4,697,088 for purposes of image inspection as the multi-layered product chip or other part is passed by the camera or the camera scans over the part. Other optical inspection apparatus are described, as further illustratives, in U.S. Letters Patent Nos. 5,058,982; 5,153,668; and 5,333,052.

In accordance with the present invention, this confusion is admirably obviated through a special use of an incident light wave length L that will cause only the intermediate insulation layer $L_2$ to fluoresce with light of a greater wavelength than the incident light, as schematically shown by the dotted return rays F in all directions back from the irregular surface of the layer $L_2$, FIG. 1C, with some fluorescent rays being collimated by the lens $L^1$ for the camera CAM including the dotted ray contributions off the vertical axis from exposed bump/depression areas of the layer not covered by the angled conductor $L_1$. By filtering all rays except those of the fluorescence greater wavelength at F1L, the reflections R of the incident wavelength of FIGS. 1A and 1B are suppressed at the filter F1L, only fluorescent light F from the intermediate layer $L_2$ will be imaged by the camera CAM. With a fluorescing intermediate layer $L_2$ of thickness sufficient to cause the fluorescing layer to be substantially totally opaqued, this results in showing the top layer pattern of conductors $C^1$ as dark in the fluorescing light image of the layer $L_2$, and, because all incident light wavelength reflections R from layers below the intermediate layer $L_2$ are masked or suppressed, they effectively disappear (shown not passing through filter FIL in FIGS. 1A and 1B), affording a clear and selective inspection of just the top pattern of conductors $C^1$.

Figure 2:
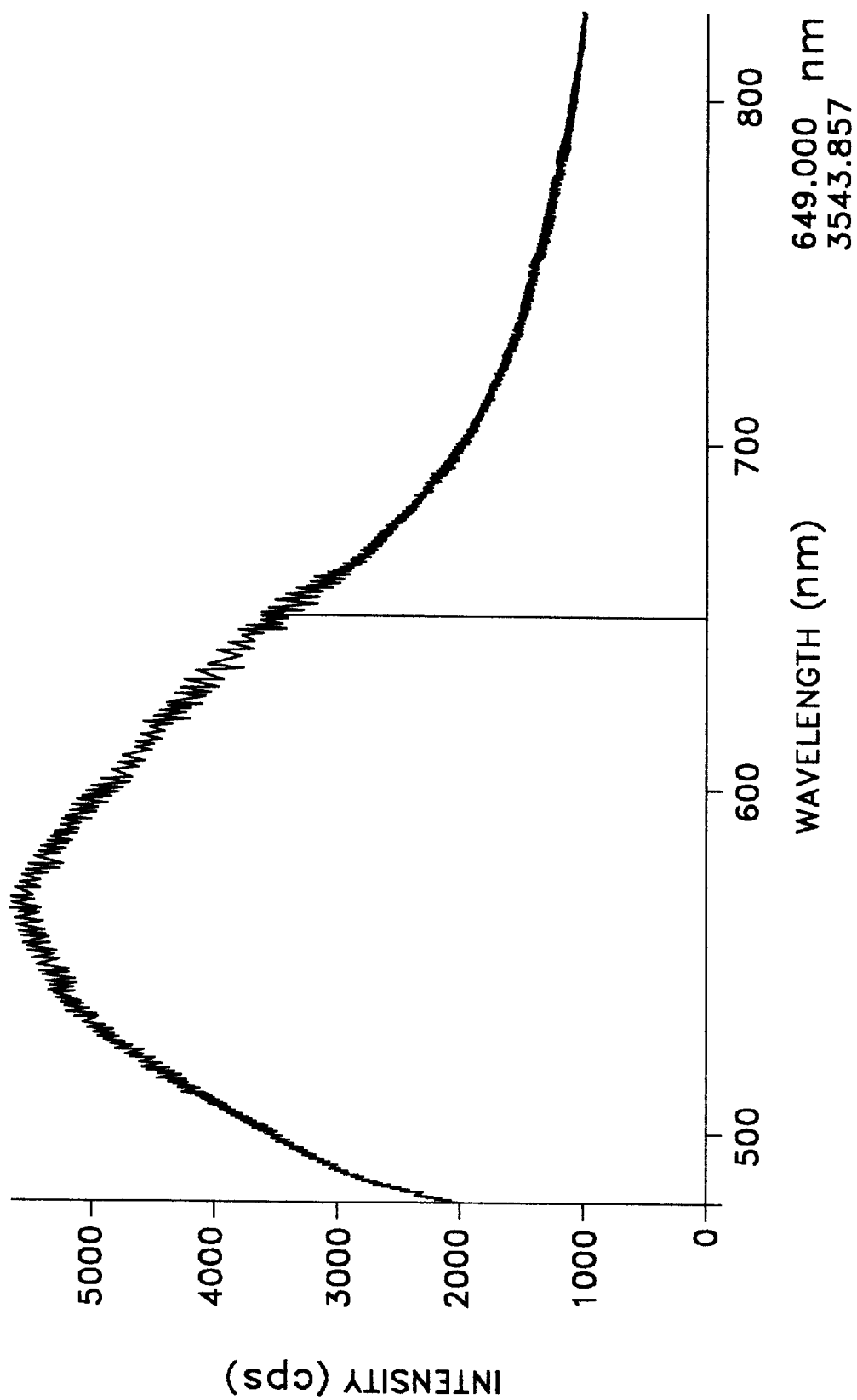
FIG. 2 is a graph illustrating a preferred fluorescent spectrum range from preferred intermediate layer insulation material in response to Argon incident light of emission line 488 nanometers.

FIG. 2, as before stated, shows the fluorescent light intensity spectrum for a preferred argon layer light source X suitable for a preferred polyimid material of transparent or translucent properties, serving as the insulation coating layer L2.

With this, a comparison of FIGS. 3 and 4 shows the efficacy of the invention. In FIG. 3, a normal white light image was produced of such a multi-layer wafer circuit, showing all the layers behind the top conductor layer. Variations in the surface of the conductor lines is also apparent. Through this technique the top layer is inspected without interference or overlay by any of the light reflections from the layers therebelow.

In this multi-layered wafer structure, the top layer appears white with many dark lines traversing it, caused by changes in topology, and with all the layers behind being also visible. It is not only very difficult to determine what the top layer is, but it is virtually impossible to find either breaks or shorts or any defect for that matter in the top conductor lines. In contrast, FIG. 4 is a photograph of the fluorescent image obtained in accordance with the invention FIG. 1C, which clearly shows the top conductors. Through this technique the top layer is inspected without interference or overlay by any of the light reflections from the layers therebelow.

In FIG. 5, another multi-chip module is shown having three layers, where it is difficult to determine what the top layer is, and with many lines and bands running through the image due to topology changes. In FIG. 6, however, using the invention (FIG. 1C), the fluorescent image very clearly distinguishing the top layer conductors to the exclusion of lower layers.

While the invention has thus far been described generally in connection with fluorescing insulation layers, preferred layers are polyimid organics fluorescing in response to 488 nanometer incident argon wavelength illumination. The fluorescence spectrum being in the range of about 500 to 700 nanometers, FIG. 2; and it is in this range that a selective filtering (F1L) is successfully effected to distinguish from any reflections from non-fluorescing materials caused by the incident light as shown in FIGS. 4 and 6. Other wavelength sources and corresponding fluorescing materials as in the above article may also be used in accordance with the phenomenon underlying the invention. Preferred bottom layers or base substrates $L_4$ are selected from ceramics, glass, epoxys, and metal. The invention, moreover, is applicable wherever there are similar multi-layered electronic or other parts requiring such top layer selectivity of inspection without confusion by reflections from lower layers. These may include, in addition to the wafers from which integrated circuit chips are formed, flat display panels, multi-chip modules, flexible circuit patches and decals and other applications.

Further modifications will also appear to those skilled in this art and all such is considered to fall within the spirit and scope of the invention as defined in the appended claims.

What is claimed is:

1. Apparatus for optically inspecting the top layer of a multi-layered electronic part comprising also intermediate and bottom layers, the top layer including a pattern of conductors-to-be-inspected disposed upon an intermediate layer of transparent or translucent insulation having irregularly spaced and shaped bumps, and with some of the conductors angularly covering only portions thereof, said apparatus having, in combination, an incident light source of predetermined wavelength to which the intermediate insulation layer and not the conductors and other layers responds by fluorescing at a different wavelength; an optical path for directing the incident light vertically upon the top layer to cause reflection of the incident light back vertically to an inspection camera for imaging the top layer therein; means for filtering out the vertically reflected light of said predetermined wavelength to prevent its receipt by the camera; a collimating lens in front of the camera for collimating fluorescent light of said different wavelength emitted from the intermediate layer in all directions with at least some fluorescent rays being collimated from directions other than vertically, resulting from fluorescent emissions along such other directions from the intermediate layer including a fluorescence contribution from uncovered portions of said irregularly spaced and shaped bumps; means for selectively creating an image in the camera, only from the collimated returned fluorescing light rays while filtering all other incident light reflections to the camera from layers above and below the bumpy intermediate layer, thereby to present the non-fluorescing pattern of conductors on the top layer as contrasting dark images in a background of the fluorescing intermediate layer image, and with reflections from below the intermediate layer effectively disappearing.

2. In an apparatus having an imaging inspection camera for optically inspecting with the aid of incident light of a predetermined wavelength the top layer of a multi-layered electronic part comprising also intermediate and bottom layers, and in which the top layer includes a pattern of conductors-to-be-inspected covering portions of an intermediate layer of transparent or translucent irregularly bumpy insulation of material that fluoresces in response to the incident light at a wavelength different from said predetermined wavelength, the bumpy layer comprising relatively flat regions between a plurality of depressions therein; and wherein it is desired that the fluorescent wavelength only be received by the camera, filtering out the incident light predetermined wavelength, to produce therein an image of the pattern of conductors that is contrastingly dark in a background of the fluorescing intermediate layer image, with light reflections from below the intermediate layer effectively disappearing, a method of enhancing the fluorescent imaging, that comprises,
angling the conductors on the intermediate layer to insure that portions only of the bump depressions are covered thereby to expose some fluorescent areas thereof to the camera; collimating the filtered light in front of the camera to gather in fluorescent rays, not only those vertically emitted from the intermediate layer, but also rays emitted along directions off the vertical as well; the collimating further enabling the reception of fluorescent ray contributions also from said exposed areas of the depressions that have been left uncovered by conductors, thereby to contribute to the fluorescent light received and imaged at the camera, and providing the fluorescent light image that achieves the contrast of the dark conductor pattern.

3. A method as claimed in claim 2 and in which the insulation layer is provided with via or contact holes which appear dark within the fluorescing image in view of the reflection through the holes from non-fluorescing layer(s) below the insulation layer.

4. A method as claimed in claim 2 and in which the bottom layer is a base substrate selected from the group consisting of ceramic, glass and metal.

5. A method as claimed in claim 4 and in which the insulation is an organic layer susceptible to fluorescing in response to the incident light wavelength.

6. A method as claimed in claim 5 and in which the organic layer comprises a polyimide.

7. A method as claimed in claim 6 and in which the incident light is provided from an argon source having predetermined emission lines at 488, and, or 514 nanometers, and the fluorescing insulation different wavelengths is in the spectrum in the range of from about 500 to 700 nanometers.

8. A method as claimed in claim 2 and in which the part is selected from the group consisting of wafers for the forming of integrated circuit chips, flat display panels, multi-chip modules, and flexible circuit patches and decals.

9. In an apparatus having an imaging inspection camera for optically inspecting with the aid of incident light of a predetermined wavelength the top layer of a multi-layered electronic part comprising also intermediate and bottom layers, and in which the top layer includes a pattern of conductors-to-be-inspected covering portions of an intermediate layer of transparent or translucent irregularly bumpy insulation of material that fluoresces in response to the incident light at a wavelength different from said predetermined wavelength, the bumpy layer comprising relatively flat regions between a plurality of depressions therein and wherein it is desired that the fluorescent wavelength only, be received by the camera, filtering out the incident light predetermined wavelength, to produce therein an image of the pattern of conductors that is contrastingly dark in a background of the fluorescing intermediate layer image, with light reflections from below the intermediate layer effectively disappearing, apparatus for enhancing the fluorescent imaging, that comprises, a pattern of conductors applied on the intermediate layer such that the conductors lie at angles to the layer and cover only portions of the bump depressions to expose some fluorescent areas thereof to the camera; collimating means disposed in front of the camera to gather in fluorescent rays, not only those vertically emitted from the intermediate layer, but also rays emitted along directions off the vertical as well; the collimating further enabling the reception of fluorescent ray contributions also from said exposed areas of the depressions that have been left uncovered by conductors, thereby to contribute to the fluorescent light received and imaged at the camera, and providing the fluorescent light-background image that achieves the contrast of the dark conductor pattern.

10. Apparatus as claimed in claim 9 and in which the light source is an argon source of predetermined emission lines at one of 488 and 514 nanometers, and the fluorescing insulation different wavelength is in the spectrum of range from about 500 to 700 nanometers.

11. Apparatus as claimed in claim 9 and in which the intermediate layer is of a polyimide.

12. Apparatus as claimed in claim 9 and in which the part is a wafer chip.

* * * * *